US012201267B2

United States Patent
Appling et al.

(10) Patent No.: US 12,201,267 B2
(45) Date of Patent: Jan. 21, 2025

(54) ENDOSCOPE CONTROL HANDLE WITH A STEERING ASSEMBLY

(71) Applicant: EnTellect Medical Holdings, Crestwood, KY (US)

(72) Inventors: Anthony Appling, Crestwood, KY (US); Ben Morris, Jeffersonville, IN (US); Brian Keith Wells, Lagrange, KY (US)

(73) Assignee: EnTellect Medical Holdings

( * ) Notice: Subject to any disclaimer, the term of this patent is extended or adjusted under 35 U.S.C. 154(b) by 1044 days.

(21) Appl. No.: 17/150,346

(22) Filed: Jan. 15, 2021

(65) Prior Publication Data

US 2021/0212553 A1    Jul. 15, 2021

Related U.S. Application Data

(60) Provisional application No. 62/961,762, filed on Jan. 16, 2020, provisional application No. 62/961,303, filed on Jan. 15, 2020, provisional application No. 62/961,493, filed on Jan. 15, 2020.

(51) Int. Cl.
    *A61B 1/005*    (2006.01)
    *A61B 1/00*     (2006.01)

(52) U.S. Cl.
    CPC ........ *A61B 1/0052* (2013.01); *A61B 1/00042* (2022.02); *A61B 1/00128* (2013.01); *A61B 1/0053* (2013.01); *A61B 1/0057* (2013.01)

(58) Field of Classification Search
    CPC . A61B 1/00128; A61B 1/0053; A61B 1/0057; A61B 1/0051; A61B 1/00066; A61B 207/00318

USPC ................................................. 600/146, 148
See application file for complete search history.

(56) References Cited

U.S. PATENT DOCUMENTS

| | | | | |
|---|---|---|---|---|
| 4,721,099 A * | 1/1988 | Chikama | ............ | A61B 1/00042 600/152 |
| 4,942,866 A * | 7/1990 | Usami | ................ | G02B 23/2476 600/148 |
| 11,654,262 B2 * | 5/2023 | Furnish | ............. | A61M 25/0136 604/95.04 |
| 2004/0059191 A1 * | 3/2004 | Krupa | ............... | A61M 25/0136 600/146 |

(Continued)

FOREIGN PATENT DOCUMENTS

| KR | 100942428 B1 | 2/2010 |
|---|---|---|
| WO | 2008046030 A2 | 4/2008 |

*Primary Examiner* — Anh Tuan T Nguyen
*Assistant Examiner* — Rynae E Boler
(74) *Attorney, Agent, or Firm* — Dickinson Wright PLLC

(57) ABSTRACT

A control handle includes a housing and at least one control wire that extends from the housing to terminate at a distal tip. A steering assembly is coupled with the at least one control wire for selectively tensioning the at least one control wire to effectuate movement of the distal tip. The steering assembly includes at least one cam that is rotatable about an axis and presents a winding surface that extends circumferentially. The at least one control wire is connected to the at least one cam. An actuator dial is rotatable about the axis and coupled with the at least one cam for rotatably driving the at least one cam from a neutral position to an actuated position to at least partially wind the control wire about the winding surface and to tension the at least one control wire for deflecting the distal tip.

19 Claims, 16 Drawing Sheets

(56) References Cited

U.S. PATENT DOCUMENTS

| | | | |
|---|---|---|---|
| 2008/0087871 A1* | 4/2008 | Schena | F16H 19/06 254/226 |
| 2010/0121147 A1* | 5/2010 | Oskin | A61B 1/0051 604/528 |
| 2011/0088498 A1 | 4/2011 | Ettwein et al. | |
| 2011/0118550 A1 | 5/2011 | Tulley | |
| 2013/0012781 A1* | 1/2013 | Kaneko | A61B 1/0057 600/148 |
| 2013/0190561 A1* | 7/2013 | Oskin | A61B 1/00124 600/110 |
| 2014/0251042 A1* | 9/2014 | Asselin | F16H 21/40 74/89 |
| 2017/0035993 A1 | 2/2017 | Quinn et al. | |
| 2017/0238787 A1* | 8/2017 | Hijihara | A61B 1/0052 |
| 2018/0028786 A1 | 2/2018 | Jungles | |
| 2019/0350440 A1* | 11/2019 | Leong | A61B 1/00066 |
| 2020/0054194 A1* | 2/2020 | Melsheimer | A61B 1/015 |

* cited by examiner

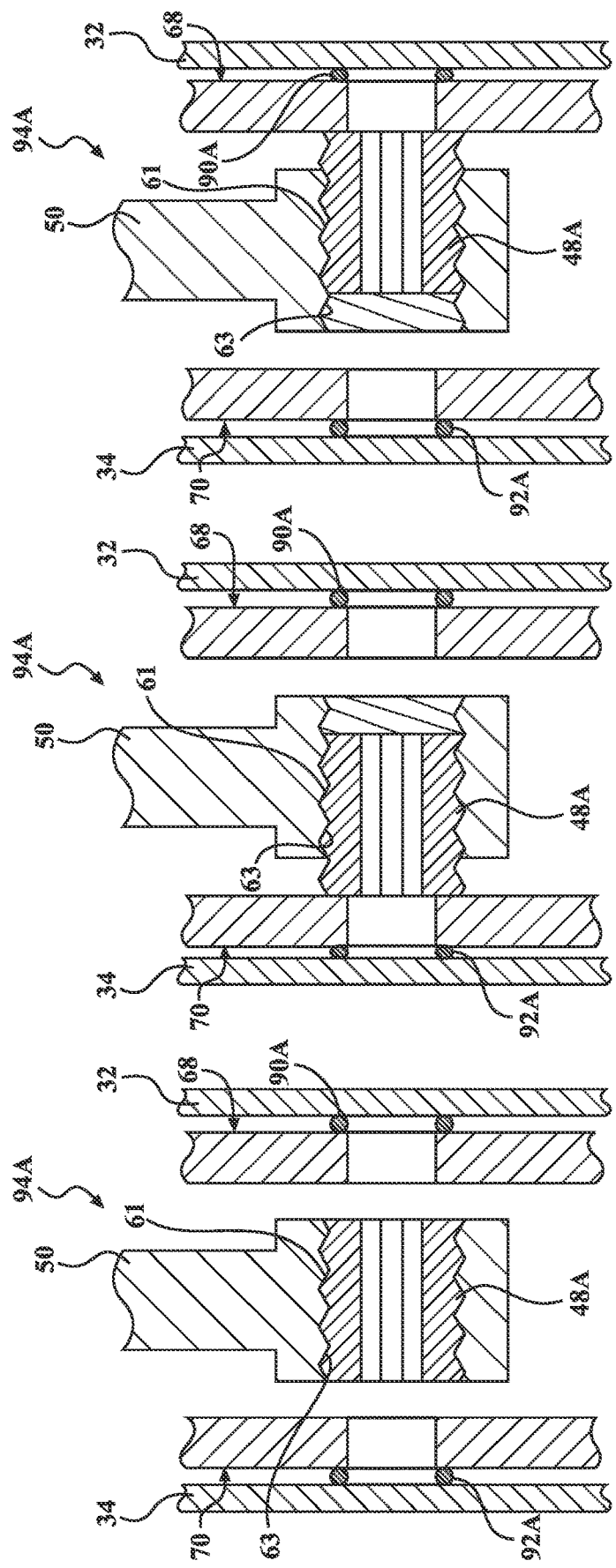

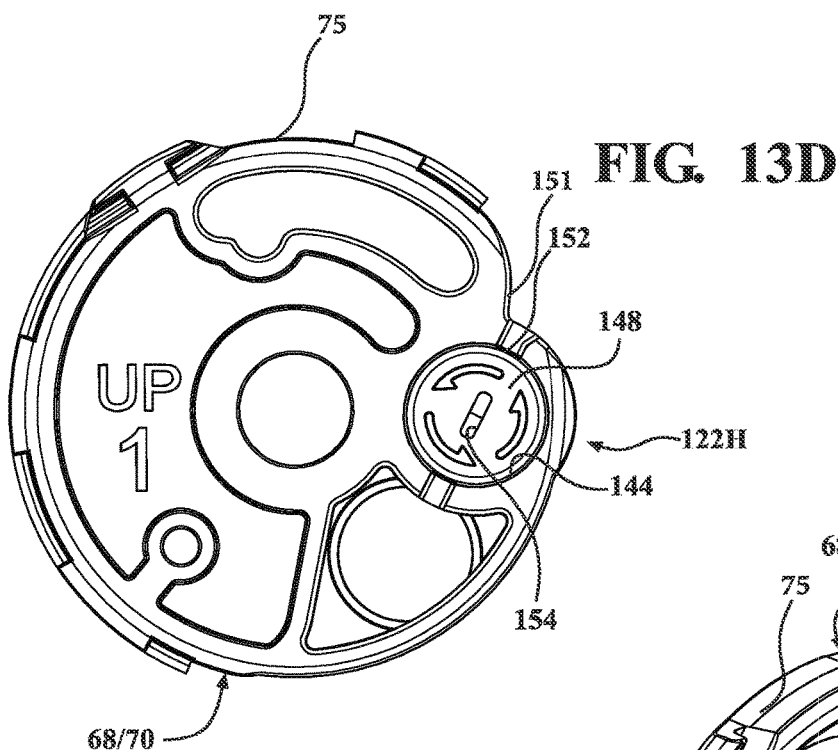
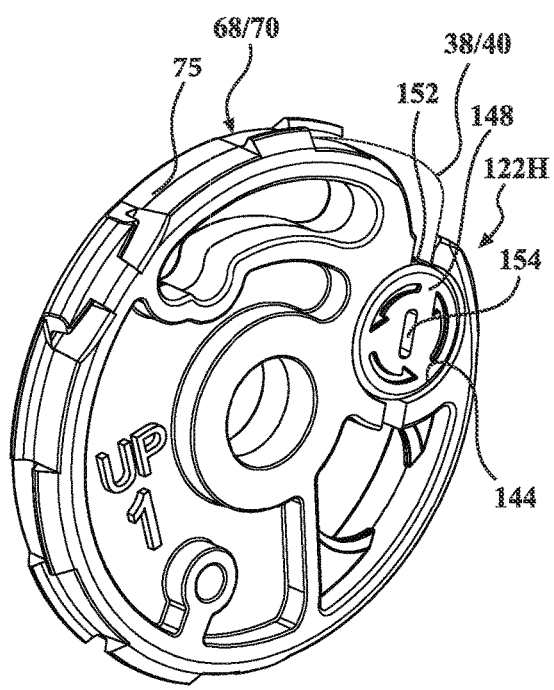
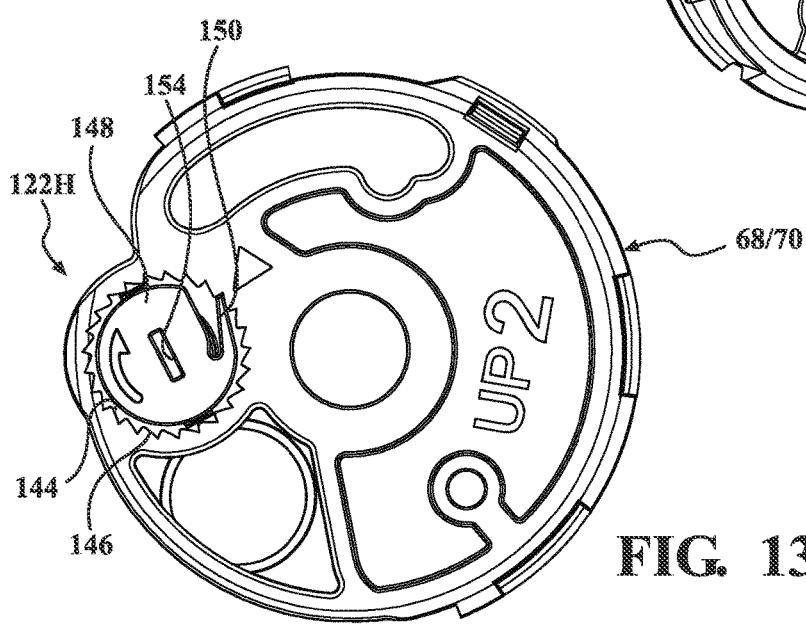

ENDOSCOPE CONTROL HANDLE WITH A STEERING ASSEMBLY

CROSS-REFERENCE TO RELATED APPLICATIONS

This application claims the benefit of U.S. Provisional Patent Application Ser. No. 62/961,303 filed on Jan. 15, 2020, titled "Endoscope Control Handle with a Steering Assembly," U.S. Provisional Patent Application Ser. No. 62/961,493 filed on Jan. 15, 2020, titled "Endoscope Control Handle with a Friction Lock," and U.S. Provisional Patent Application Ser. No. 62/961,762 filed on Jan. 16, 2020, titled "Endoscope Control Handle with a Control Wire Tensioning Mechanism," the entire disclosures of which are hereby incorporated by reference in their entirety.

TECHNICAL FIELD

The present disclosure relates to a control handle for a medical interventional device, such as an endoscope. More particularly, the present disclosure relates to a control handle including a steering assembly to provide movement of a distal tip in response to movement of an actuator dial by an operator.

BACKGROUND

An endoscope is a medical instrument for visualizing the interior of a patient's body. Endoscopes can be used for a variety of different diagnostic and interventional procedures, including colonoscopy, bronchoscopy, thoracoscopy, laparoscopy, ureteroscopy, and video endoscopy. Endoscopes typically have a control handle which is configured to allow a user to control a position of a distal tip during the procedure by tensioning a series of wires that extend from the control handle to the distal tip. There remains a need for improvements to such endoscope control handles.

SUMMARY OF THE INVENTION

A control handle for an interventional device includes a housing and at least one control wire that extends from the housing to terminate at a distal tip. A steering assembly is coupled with the at least one control wire in the housing for selectively tensioning the at least one control wire to effectuate movement of the distal tip. The steering assembly includes at least one cam that is rotatable about an axis and presents a winding surface that extends circumferentially about the axis. At least one control wire is connected to the at least one cam. The steering assembly further includes an actuator dial rotatable about the axis and operably coupled with the at least one cam for rotatably driving the at least one cam from a neutral position to an actuated position to at least partially wind the control wire about the winding surface and to tension the at least one control wire for deflecting the distal tip in response to rotation of the actuator dial by a user.

The subject control handle provides displacement of the distal tip in a simple, consistent and ergonomic manner. The subject control handle is also simple in design, compact, lightweight and inexpensive and easy to manufacture.

BRIEF DESCRIPTION OF THE DRAWINGS

Other aspects of the present disclosure will be readily appreciated, as the same becomes better understood by reference to the following detailed description when considered in connection with the accompanying drawings wherein:

FIGS. 5C-5E are front, cross-sectional partial views of the second embodiment of the friction lock, illustrating the thrust bearing disposed in various axial positions;

FIG. 13D is a right side view of the cam of the fourth embodiment of the tensioning mechanism;

FIG. 13E is a right side perspective view of the cam of the fourth embodiment of the tensioning mechanism; and FIG. 13F is a left side view of the cam of the fourth embodiment of the tensioning mechanism.

DETAILED DESCRIPTION OF THE EXEMPLARY EMBODIMENTS

In the following description, details are set forth to provide an understanding of the present disclosure. In some instances, certain systems, structures and techniques have not been described or shown in detail in order not to obscure the disclosure.

Figure 1:
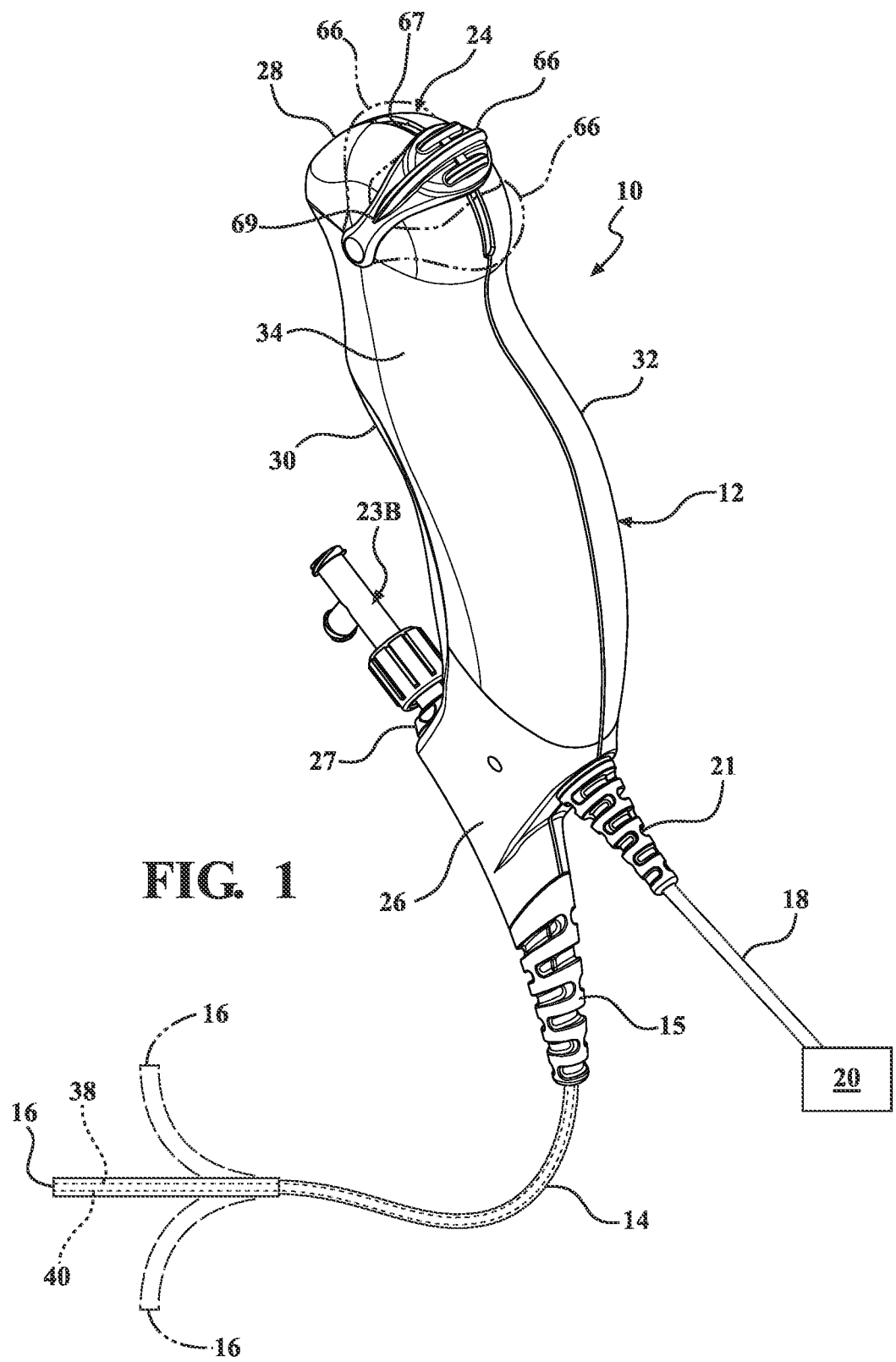
FIG. 1 is a perspective view of an example embodiment of an endoscope control handle.

Referring to the figures, wherein like numerals indicate corresponding parts throughout the several views, a control handle 10 for a medical interventional device is generally shown. The subject control handle 10 is described herein for use with an endoscope, however, it should be appreciated that it could be used in association with other medical interventional devices. As illustrated in FIG. 1, the endoscope control handle 10 includes a housing 12 which extends in a longitudinal direction between a proximal end 28 and a distal end 26, and includes a gripping region 30 located between the proximal and distal ends 28, 26. The gripping region 30 is shaped to receive a palm and fingers of a user to provide easy, comfortable, and ergonomic gripping of the housing 12 by the user during use of the endoscope control handle 10. The housing 12 is comprised of a first shell 32 and a second shell 34 that are generally mirror images of one another, with minor variances, and coupled with one another along a plane to collectively define a hollow compartment 36. An axle 42 extends from the first shell 32 in the compartment 36 along a rotational axis A, and terminates at an open end 44. An attachment mechanism 46 couples the first and second shells 32, 34 to one another. According to the example embodiment, the attachment mechanism 46 is a bolt 46 that is threadedly received by the open end 44 of the axle 42 and threaded to the second shell 34 for securing the first shell 32 to the second shell 34. Additional fasteners 47 may be provided for securing the shells 30, 32 to one another at other locations. It should be appreciated that various other attachment mechanisms could be employed, e.g., snap-mating features.

Figure 2:
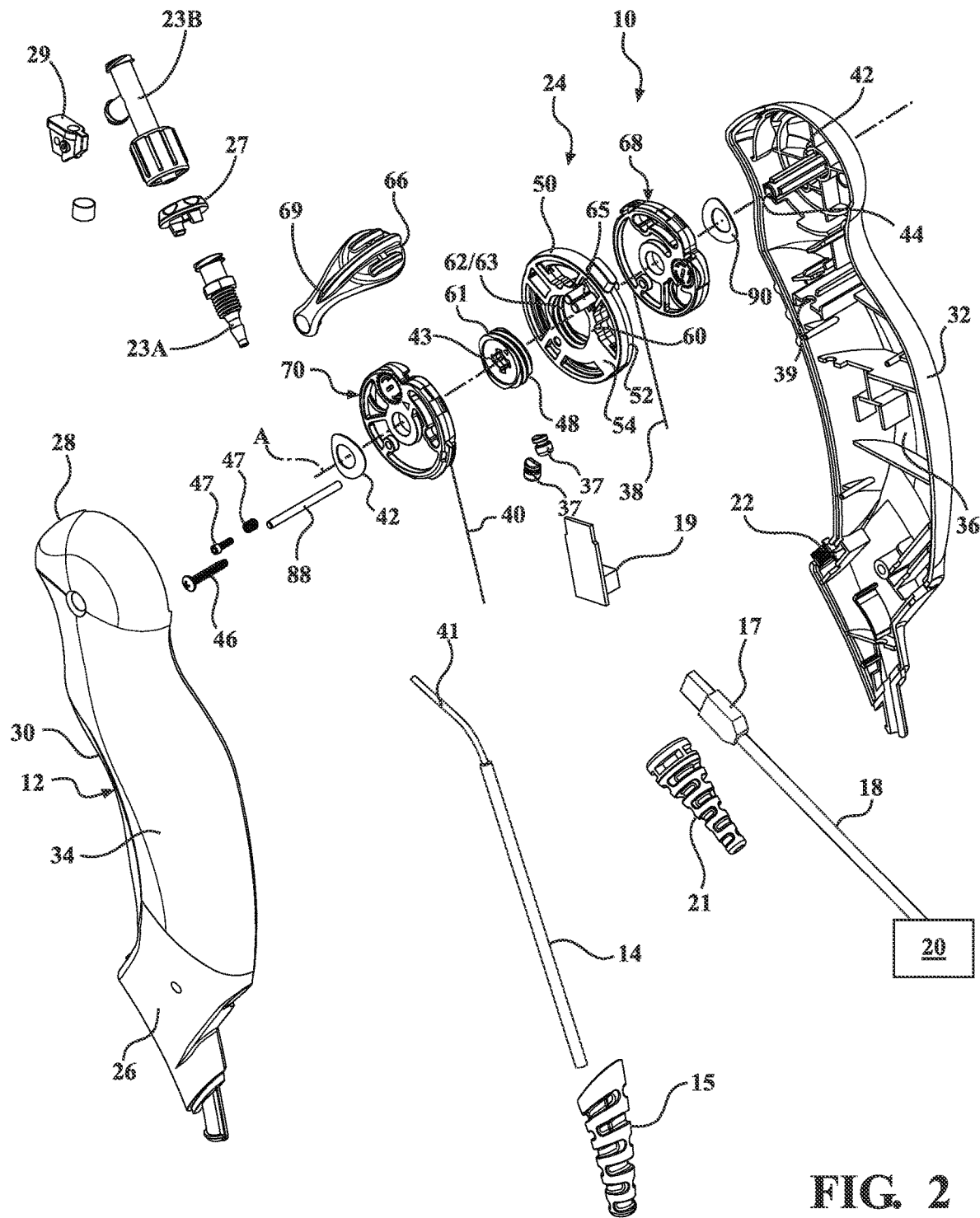
FIG. 2 is an exploded view of the endoscope control handle.

An endoscope tube 14 extends from the compartment 36 of the housing 12 and terminates at a distal tip 16 outside of the housing 12 for being located inside a patient's body for diagnostic and interventional procedures. An anchor 29 secures the endoscope tube 14 to the housing 12 inside the compartment 36. A lumen 41 is received by the endoscope tube 14 and extends along a length of the endoscope tube 14 from the compartment 36 of the housing 12 to the distal tip 16 for operating as a working channel to provide access of devices to the distal tip 16. A first strain relief 15 surrounds the endoscope tube 14 at an interface of the endoscope tube 14 and the housing 12 to provide flexibility to the endoscope tube 14, and for protecting the endoscope tube 14 from kinking. An umbilical cable 18 extends from the housing 12 for being coupled with a processing device 20 for receiving data obtained by devices at the distal tip 16. The processing device 20 may include various types of electronics configured to display image data or perform various other analytical functions. As shown in FIG. 2, the umbilical cable 18 may include a connector 17 inside the housing for being connected with a data card 19. A second strain relief 21 is attached to the housing 12 and surrounds the umbilical cable 18. Like the first strain relief 15, the second strain relief 21 provides flexibility to, and protects the umbilical cable 18 from kinking and pulling forces. A port 23A, 23B is located outside of the housing 12 and is connected to an inlet 22 of the housing 12 and lumen 41 for accommodating the attachment of user prescribed accessories and for providing access for insertion of tools (e.g., diagnostic and therapeutic devices) and irrigation into the lumen 41. The port 23A, 23B is comprised of a first tube segment 23A that extends into the inlet 22 of the housing 12 and receives the lumen 41, and a second tube segment 23B that is coupled with an opposing end of the first tube segment 23A. A securement ring 27 is positioned about the first tube segment 23A outside of the housing 12 for preventing rotation of the first tube segment 23A to prevent disconnection of the port 23A, 23B from the housing 12.

As shown in FIGS. 1 and 2, at least one control wire 38, 40 (or cable) extends from the compartment 36 of the housing 12 into the endoscope tube 14 about the lumen 41 and ultimately terminates at the distal tip 16. According to the example embodiment, the at least one control wire 38, 40 includes a first control wire 38 and a second control wire 40 ultimately terminating at diametrically opposite portions of the distal tip 16. With reference to FIG. 1, the distal tip 16 is configured to deflect from a neutral position (solid line in FIG. 1) to at least one deflected position (shown in broken lines in FIG. 1) in response to tensioning of the control wires 38, 40. According to the example embodiment and as further shown in FIG. 1, the distal tip 16 is configured to deflect in two directions and into two deflected positions. A mounting body 37 may be positioned about each of the wires 38, 40 and connectable to mounting features 39 of the housing 12 for locating the wires 38, 40 at specific locations in the compartment 36.

Figure 3:
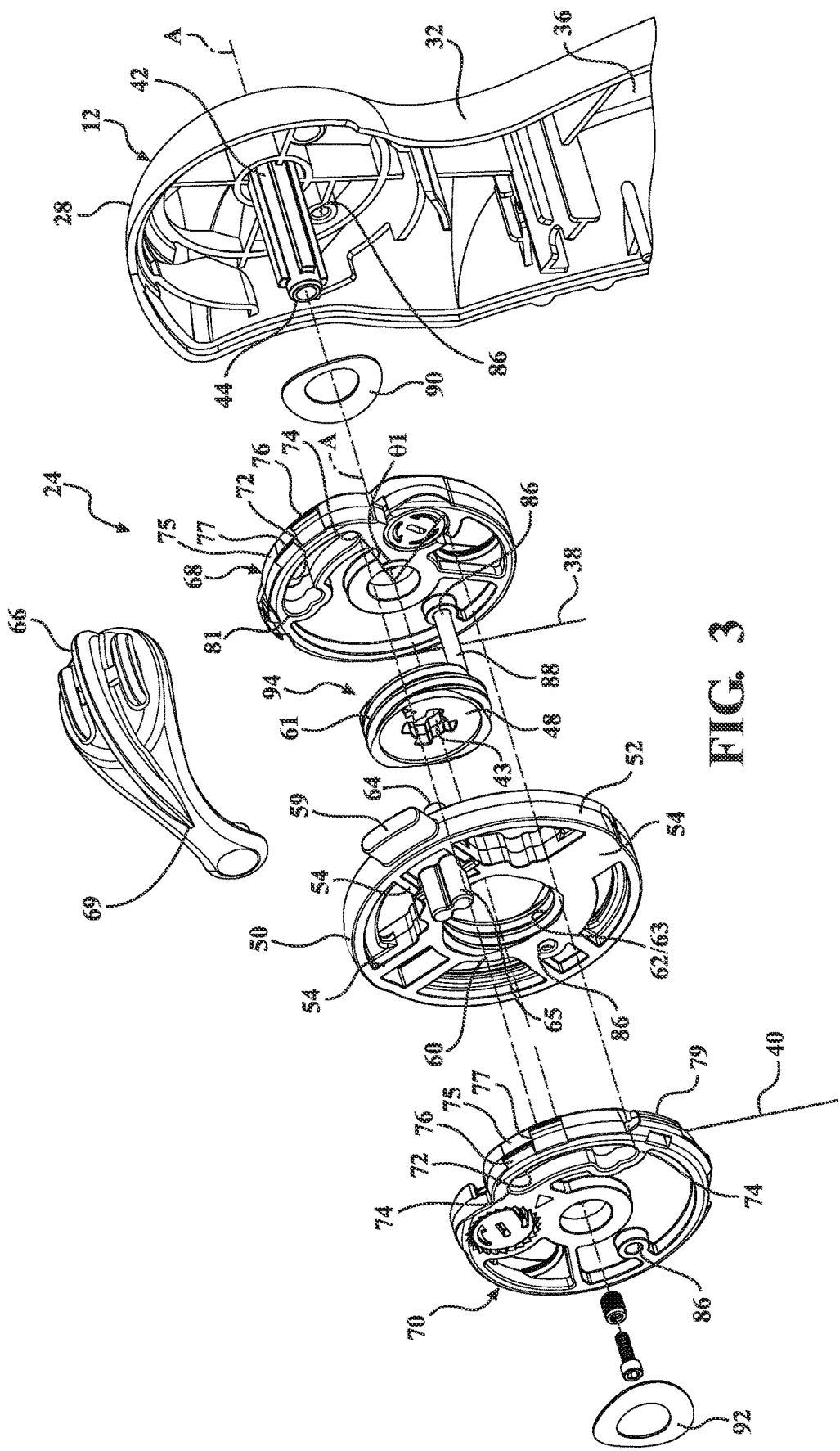
FIG. 3 is an exploded view of a steering assembly of the endoscope control handle and illustrating a first embodiment of a friction lock.

With reference to FIG. 3, a steering assembly 24 is located adjacent to the proximal end 28 of the housing 12 to control the tensioning of the first and second control wires 38, 40 to effectuate the deflecting movement of the distal tip 16. The steering assembly 24 includes an actuator dial 50 that has an outer ring portion 52 and an inner ring portion 60 located radially inwardly of the outer ring portion 52. The actuator dial 50 is rotatable about the axle 42 along a central channel 62 defined by the inner ring portion 60. The actuator dial 50 further can include a plurality of spokes 54 that extend radially between, and connect the outer and inner ring portions 56, 60.

Figure 4:
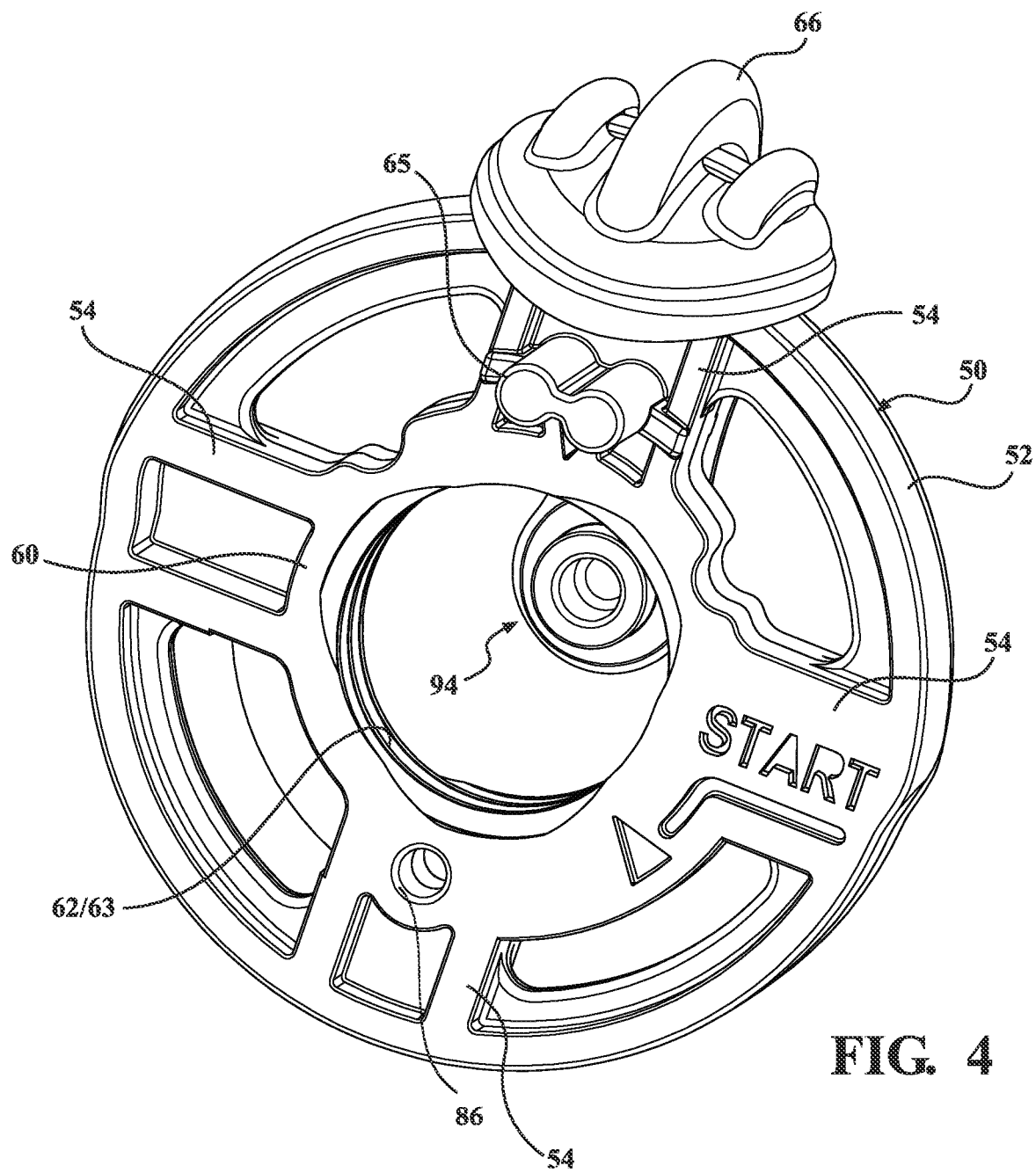
FIG. 4 is a side perspective view of the actuator dial of the steering assembly and further illustrating the first embodiment of the friction lock.

As best shown in FIG. 4, the actuator dial 50 further includes a first cam follower 64 and a second cam follower 65 that are spaced radially outwardly from the axis A, and extend axially away from one another on axially opposite sides of one of the spokes 54 in axial alignment with one another. It should be appreciated that the cam followers 64, 65 could extend from various locations of the actuator dial 50 without departing from the scope of the subject disclosure.

A connecting arm 59 extends radially outwardly from the outer ring portion 52 of the actuator dial 50 through a pivoting channel 67 defined along the proximal end 28 of the housing 12. A thumb grip 66 is located outside of the housing 12 and is coupled with the connecting arm 59 for allowing a user to rotate the actuator dial 50 about the rotational axis A in a comfortable, ergonomic manner. A connecting leg 69 extends from the thumb grip 66 along a side of the proximal end 28 of the housing 12 and is pivotably coupled to the housing 12 along the axis A for further coupling the thumb grip 66 with the housing 12 and for further accommodating rotation of the actuator dial 50. It should be appreciated that the thumb grip 66 can be connected to the actuator dial 50 in various other ways without departing from the scope of the subject disclosure.

As best shown in FIG. 3, the steering assembly 24 further includes at least one cam 68, 70 rotatable about the axle 42 and located axially between one of the shells 32, 34 of the housing and the actuator dial 50. According to the example embodiment, the steering assembly 24 includes a first cam 68 that is rotatable about the axle 42 and located axially between the first shell 32 of the housing 12 and the actuator dial 50, as well as a second cam 70 that is rotatable about the axle 42 and located axially between the second shell 34 of the housing 12 and the actuator dial 50. The first and second cams 68, 70 each define a generally arc-shaped channel 72 extending arcuately about the axis between a driven end 74 and an undriven end 81. The first cam follower 64 of the actuator dial 50 is received by and moveable within the channel 72 of the first cam 68, and the second cam follower 65 is received by and moveable within the channel 72 of the second cam 70.

The first and second cams 68, 70 are each generally disc-shaped to present a winding surface 75 on an outer circumference for winding the first and second control wires 38, 40 about a respective one of the first and second cams 68, 70 during rotation. A plurality of tabs 76 extend radially outwardly from the winding surface 75 of each of the first and second cams 68, 70 in circumferentially spaced relationship with one another and are arranged to guide the first and second control wires 38, 40 along the winding surface 75. At least one of the tabs 76 may present a radially outer barrier 79 for preventing radial outward movement of the control wires 38, 40. The first control wire 38 is adjustably secured to the first cam 68 and the second control wire 40 is adjustably secured to the second cam 70. As will be discussed in further detail below, various methods of securing the first and second control wires 38, 40 to the first and second cams 68, 70 may be employed. The first and second cams 68, 70 are oriented in axially opposite directions relative to one another such that the first and second control wires 38, 40 are wound about the first and second cams 68, 70 in opposite rotational directions. For example, as shown in FIG. 3, the first control wire 38 may be wound in a counter-clockwise direction about the first cam 68 and the second control wire 40 may be wound in a clockwise direction around the second cam 70. The directions of the cams 68, 70 and control wires 38, 40 may be reversed.

During use of the control handle 10, the first and second cams 68, 70 and actuator dial 50 are initially located in a neutral position during which there is no tension on the first and second control wires 38, 40. This correlates with the position of the distal tip 16 shown in solid lines in FIG. 1. The first and second cams 68, 70 are rotatable in response to the first and second cam followers 64 engaging the driven ends 74 of the channels 72 during rotation of the actuator dial 50 away from the neutral position to an actuated position for tensioning the first and second control wires 38, 40, and thus providing displacement of the distal tip 16 as illustrated in dashed lines in FIG. 1. As shown in FIG. 1, a driven end 74 of the channel 72 of the first cam 68 is circumferentially/rotationally offset from the undriven end 81 of the channel 72 of the second cam 70 at a predetermined angle $\theta 1$ in the neutral position such that rotational movement of the first cam 68 in a first rotational direction by engagement of the first cam follower 64 against the driven end 74 of the channel 72 of the first cam 68 corresponds with movement of the second cam follower across the channel 72 of the second cam 70 from the driven end 74 toward the undriven end 81 without providing rotational movement of the second cam 70, and vice-versa. In other words, during rotation of the actuator dial 50 in the first rotational direction, the first cam follower 64 engages the driven end 74 of the channel 72 of the first cam 68 to effectuate rotation of the first cam 68 while the second cam follower 64 travels within the channel 72 of the second cam 70 in spaced and non-engaging relationship with the undriven end 81. As such, rotation of the actuator dial 50 in the first rotational direction causes rotation of the first cam 68 in the first rotational direction and tensioning of the first control wire 38 without tensioning the second control wire 40, thereby providing deflecting of the distal tip 16 in a first direction, while rotation of the actuator dial 50 in the second rotational direction causes rotation of the second cam 70 and tensioning of the second control wire 40 without tensioning the first control wire 38, thereby providing deflecting of the distal tip 16 in a second direction.

According to an alternate embodiment, the driven end 74 of the channel 72 of the first cam 68 could be axially aligned with undriven end 81 of the second cam 80, and the cam followers 64 could be circumferentially offset from one another at the predetermined angle $\theta 1$ to provide the same effect. Rotating the actuator dial 50 back to its neutral position allows tension in the wires 38, 40 to rotate or retract/pull the cams 68, 70 back to their neutral positions. As such, during use, an operator is able to deflect the distal tip 16 in the two directions by rotating the actuator dial 50 in first and second rotational directions.

As further shown in FIG. 3, the first shell 32, second shell 34, first cam 68, second cam 70 and actuator dial 50 each define a respective alignment hole 86. During assembly of the control handle 10, the alignment holes 86 are axially aligned when the first and second cams 68, 70 and actuator dial 50 are in the neutral position, with the driven end 74 of the channel 72 of the first cam 68 rotationally offset from the undriven end 81 of the channel 72 of the second cam 70 at the aforementioned predetermined angle $\emptyset_1$. While in this position, the alignment holes 86 receive an alignment pin 88 to ensure that the first shell 32, second shell 34, first cam 68, second cam 70 and actuator dial 50 are aligned in this manner. After assembly, the alignment pin 88 is removed. As previously noted, while in this neutral position, there is neutral tension on the first and second control wires 38, 40—this minimizes any dead space or lag at the distal tip 16 when the actuator dial 50 is rotated.

As illustrated in FIGS. 3-9C, the steering assembly 24 further includes a friction lock 94-94D for preventing tension of the wires 38, 40 from providing undesired rotation of the cams 68, 70 and actuator dial 50 back to the neutral position upon release of the actuator dial 50 by a user during operation of the control handle 10. As such, the release of tension from the control wires 38, 40 is only provided in response to movement of the actuator dial 50 back to the neutral position by a user. Accordingly, the friction lock 94 allows a user to release their thumb from the thumb grip 66 of the actuator dial 50 while the actuator dial 50 is rotated toward one of the actuated positions and still maintain a specific deflection of the distal tip 16. In other words, the friction lock 94-94D eliminates the need to manually hold the actuator dial 50 toward the actuated positions, thus reducing the likelihood of inadvertent movements of the distal tip 16 which could otherwise lead to injuries or improper operations, while also providing a more comfortable ergonomic experience for the operator.

According to first and second embodiments of the friction lock shown in FIGS. 3-5E, the friction lock 94, 94A includes a thrust bearing 48 that is positioned about and keyed to the axle 42 along a central passage 43 such that rotation is fixed or prevented relative to the axle 42 while translating axial movement relative to the axle 42 is permitted. The central channel 62 of the inner ring portion 60 presents a plurality of second threads 63 that are threaded with the first threads 61 of the thrust bearing 48 to provide linear translational movement of the thrust bearing 48 in response to rotation of the actuator dial 50 about the thrust bearing 48. The friction lock 94, 94A further includes a first compression element 90, 90A positioned about the axle 42 and located axially between the first shell 32 of the housing 12 and the first cam 68, and a second compression element 92, 92A is positioned about the axle 42 and located axially between the second shell 34 and the second cam 70. In a preferred embodiment, the compression elements 90 are comprised of wave washers 90 (FIG. 3), however, the compression elements 90, 90A could also be comprised of other materials, such as the O-rings 92A shown in FIGS. 5C-5E. According to either arrangement, the compression elements 90, 92, 90A, 92A may each be received in a recessed channel along axial sides of the cams 68, 70 for assisting in orienting the compression elements 90, 92, 90A, 92A concentrically about the rotational axis A.

Figure 5B:
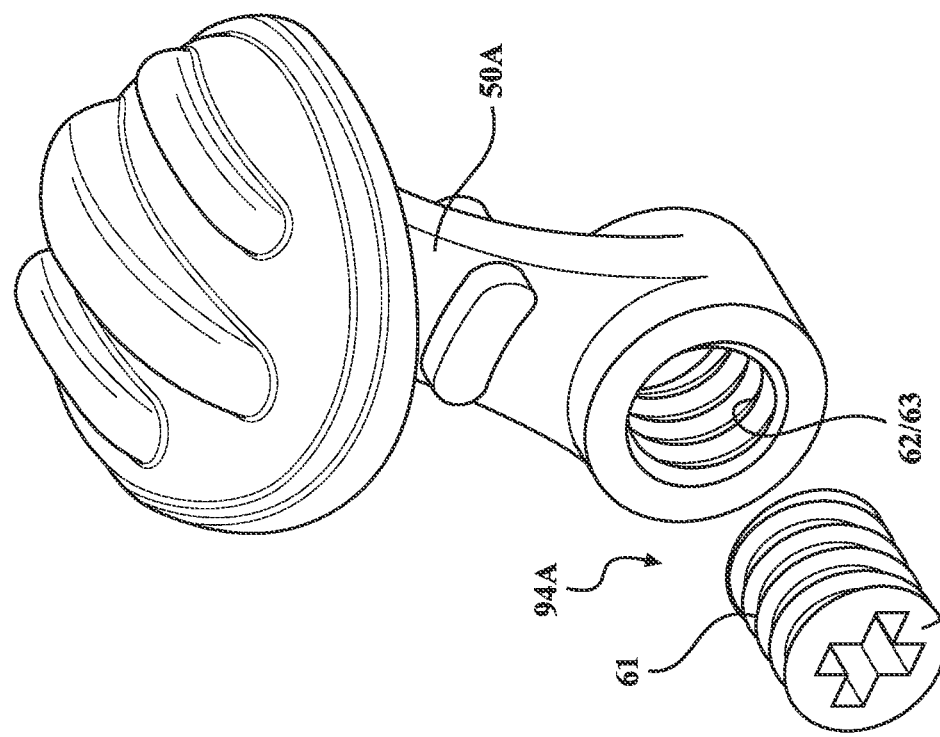
FIG. 5B an exploded perspective view of the second embodiment of the friction lock illustrating a thrust bearing.
Figure 5A:
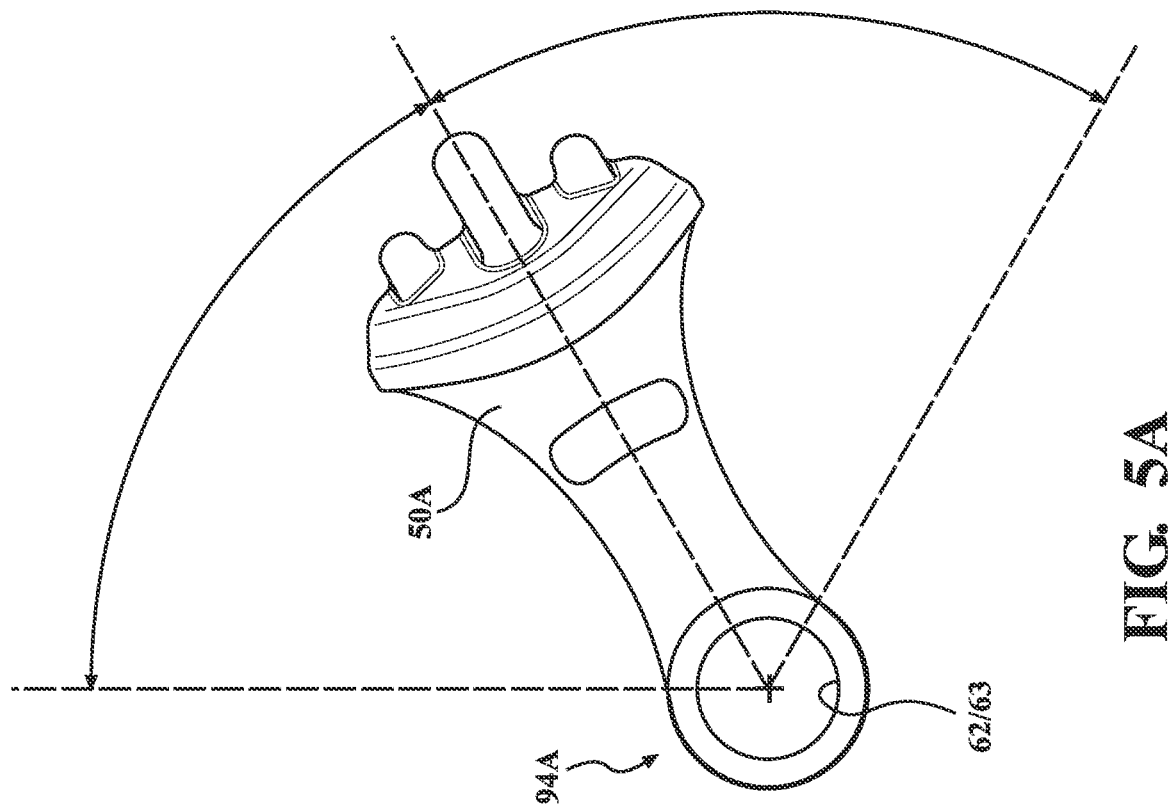
FIG. 5A is a side view of an actuator dial of a second embodiment of the friction lock.

During use of the control handle 10, while the actuator dial 50 is in the neutral position (e.g., FIG. 5C) the compression elements 90, 92, 90A, 92A provide minimal resistance to rotation of the cams 68, 70 due to the fit between the cams 68, 70 and shells 32, 34 of the housing 12. Rotation of the actuator dial 50, 50A in the first rotational direction causes the thrust bearing 48, 48A to move axially toward a first of the rotating cams 68, 70 by way of the threads 61, 63 (FIG. 5E), while rotation of the actuator dial 50 in the second rotational direction causes the thrust bearing 48, 48A to move axially toward the other of the rotating cams 68, 70 (FIG. 5D). This axial displacement applies an axial load to the respective cam 68, 70, changing its axial position linearly along the along the axle 42 toward the adjacent shell 32, 34. This position change creates an interference condition between the respective cam 68, 70, the compression element 90, 92, 90A, 92A and the adjacent outer shell 32, 34 of the housing 12 (as shown in FIGS. 5D and 5E). Increased rotation of the actuator dial 50 proportionally increases a compression stack-up on the respective compression element 90, 92, 90A, 92A. This compression stack-up creates the friction force that holds the cam 68, 70 in place when no load is being applied to the actuator dial 50 by the user, thus maintaining a displacement of the distal tip 16 at any particular position. The tension force required to create the displacement is directly proportional to the amount of displacement, and the compressive friction force applied to the cam 68, 70 by the mechanism is likewise proportional. When the actuator dial 50 is returned to the neutral position, the thrust bearing 50 returns to a central position and thus no compressive force is applied by the thrust bearing 48, 48A. The friction lock 94, 94A works as described in the opposite direction. In this way, the friction lock 94, 94A is passive and does not require controls or additional specific inputs from the user.

Figure 6C:
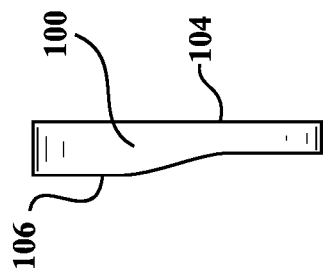
FIG. 6C is a front view of one of the thrust rings of the third embodiment of the friction lock.
Figure 6B:
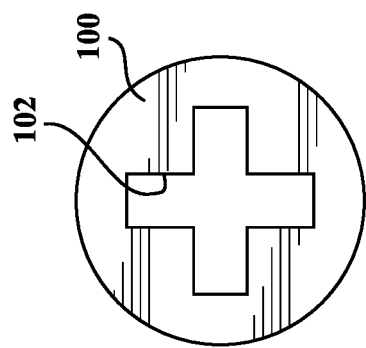
FIG. 6B is a side view of one of the thrust rings of the third embodiment of the friction lock.
Figure 6A:
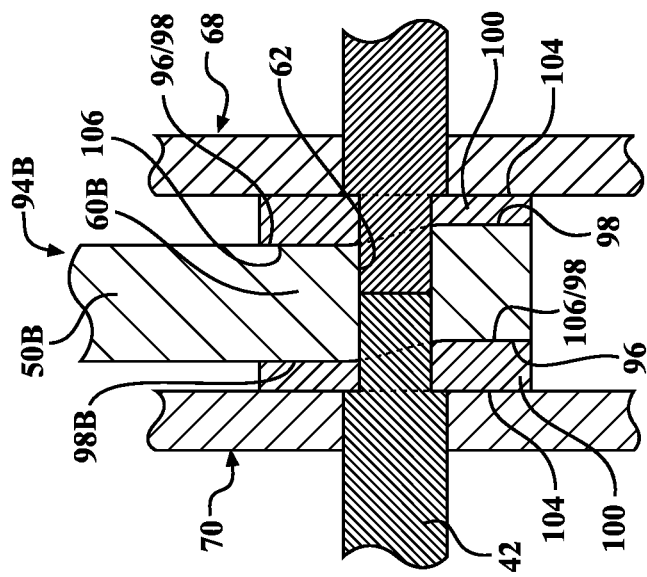
FIG. 6A is a front cross-sectional partial view of the third embodiment of a friction lock illustrating an arrangement of thrust rings.
Figure 7A:
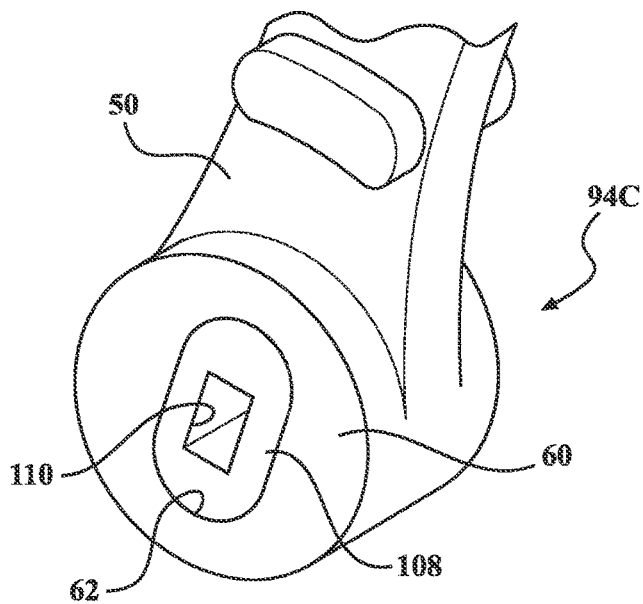
FIG. 7A is a fragmentary side perspective view of a portion of an embodiment of the steering assembly illustrating a fourth embodiment of the friction lock.
Figure 7B:
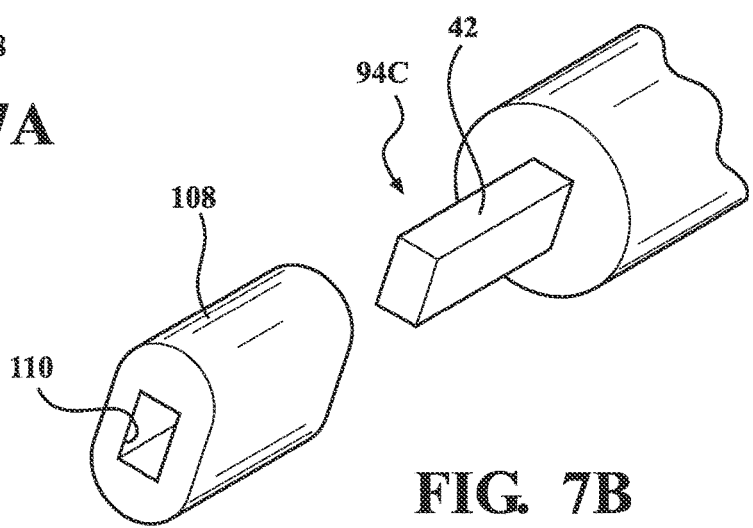
FIG. 7B is a perspective exploded view of the fourth embodiment of the friction lock illustrating an axle and an elastomeric gasket.
Figure 7C:
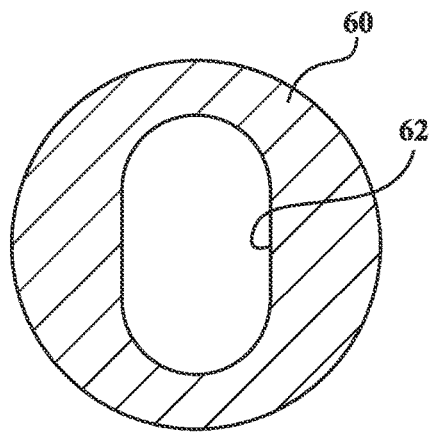
FIG. 7C is a side view of an inner ring portion of an actuator dial of the fourth embodiment of the friction lock.
Figure 7D:
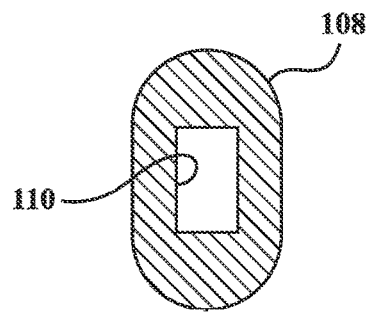
FIG. 7D is a side view of the elastomeric gasket of the fourth embodiment of the friction lock.
Figure 8A:
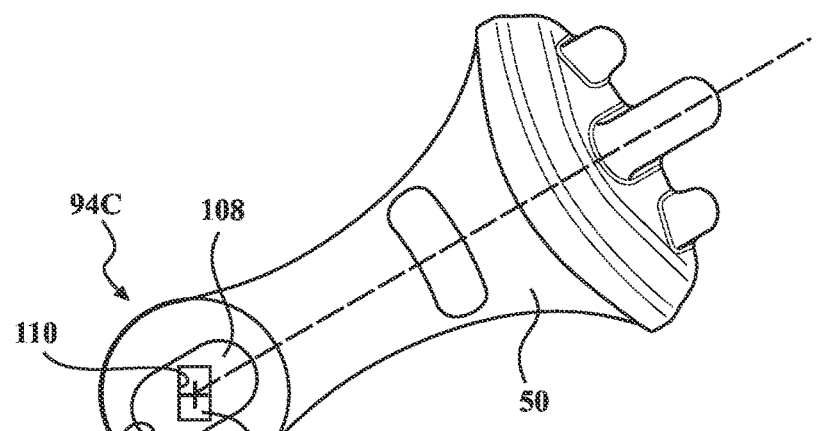
FIG. 8A is a side view of the fourth embodiment of the friction lock disposed in a first position.
Figure 8B:
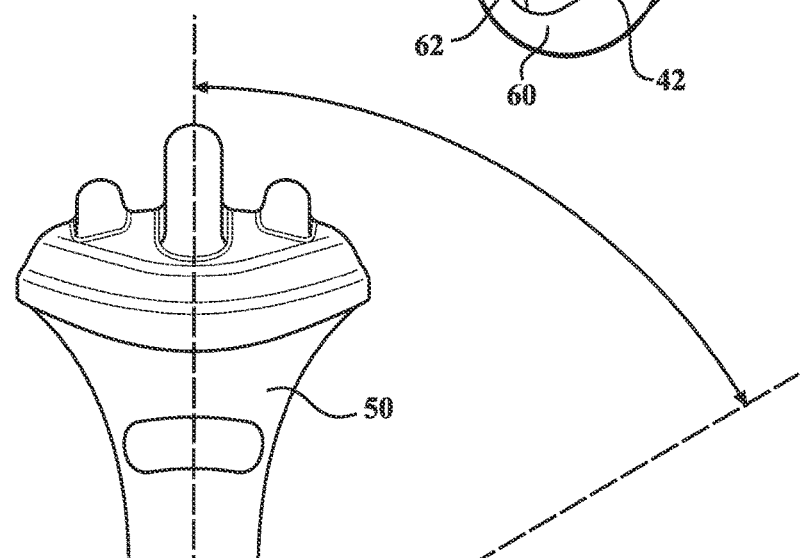
FIG. 8B is a side view of the fourth embodiment of the friction lock disposed in a second position.
Figure 8C:
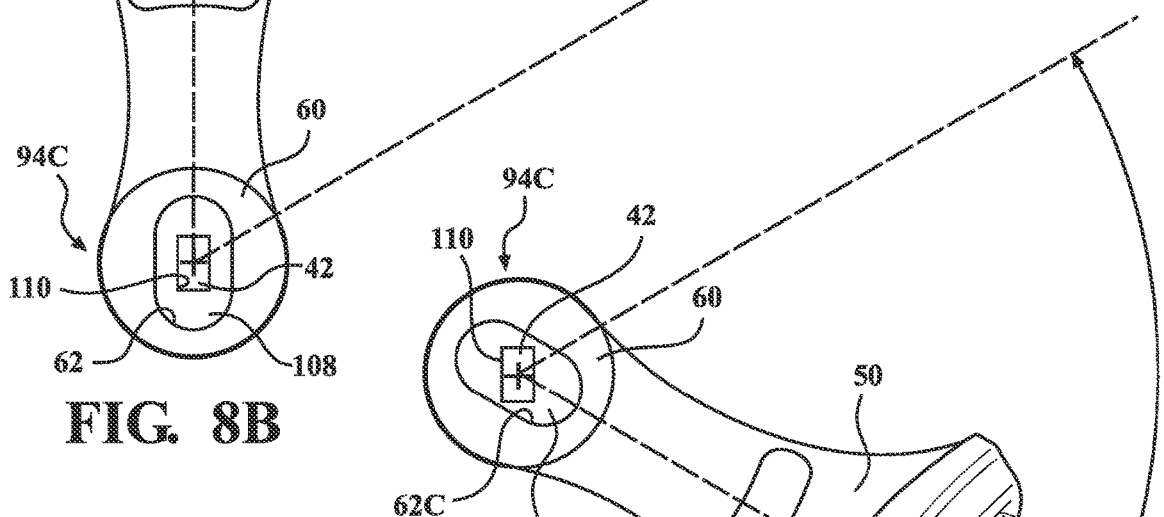
FIG. 8C is a side view of the fourth embodiment of the friction lock disposed in a third position.

In accordance with a third embodiment of the friction lock 94B shown in FIGS. 6A-6C, the thrust bearing 48, 48A is replaced by a wave washer shaped inner ring portion 60B of the actuator dial which includes a pair of opposing axial faces 96 thereof each presenting at least one sloped protrusion 98 that extends axially. The inner ring portion 60B further has an unthreaded central channel 62 which receives the axle 42 and allows the actuator dial 50 to rotate about the axle 42. The friction lock 94B further includes a pair of thrust rings 100 that are keyed to the axle 42 such that they are unable to rotate about the axle 42B, but able to translate axially along the axle 42. More particularly, as best illustrated in FIG. 6C, each of the thrust rings 100 has a central passage 102 that has a non-circular shape that matches an outer profile of the axle 42 in order to allow axial movement of the thrust rings 100 while prohibiting rotational movement thereof. In the example embodiment, the central passage 102 and axle 42 each have a generally "plus-sign" shape, however, other shapes could be utilized. One of the thrust rings 100 is located axially between the actuator dial 50B and the first cam 68, and the other is located axially between the actuator dial 50 and the second cam 70. Each of the thrust rings 100 has a first axial face 104 that is generally planar and a second axial face 106 that presents at least one sloped protrusion 98 that extends axially. The at least one sloped protrusion of the second axial face 106 of each of the thrust rings 100 are shaped opposite the protrusions sloped protrusions 98 of the inner ring portion 60B such that when the actuator dial 50B is in the neutral position, the thrust ring 100 overlies one of the axial faces 96 of the inner ring portion 60B with the protrusions 98 of the thrust rings 100 and inner ring portion 60B circumferentially spaced from one another such that the second axial face 106 of the thrust ring 100 nests with one of the axial faces 96 of the actuator dial 50B. Upon rotation of the actuator dial 50B by the operator, the protrusions 98 of the actuator dial 50B and thrust rings 100 becoming increasingly circumferentially aligned with one another, thus driving the thrust bearings 100 axially against the cams 68, 70, thereby creating a frictional force between the actuator dial 50, thrust rings 100 and cams 68, 70. Increased rotation of the actuator dial 50 proportionally increases the frictional force as the peaks of the protrusions 98 become more aligned with one another. Similar to the previously described embodiment of the friction lock 94, this friction force holds the cams 68, 70 in place when no load is being applied to the actuator dial 50 by the user, thus maintaining a displacement of the distal tip 16 at any particular position.

In accordance with a fourth embodiment of a friction lock 94C shown in FIGS. 7A-8C, the thrust bearing is replaced with an elastomer gasket 108 that is keyed to the axle 42.

Furthermore, the central channel 62 of the inner ring portion 60 of the actuator dial 50 is disposed about the elastomer gasket 108 for generating a frictional force between the elastomer gasket 108 and the inner ring portion 60 during rotation of the actuator dial 50. More particularly, the elastomer gasket 108 has a central orifice 110 that has a non-circular shape that matches an outer profile of the axle 42 in order to prevent rotation of the elastomer gasket 108 about the axle 42. In the example embodiment, the central orifice 110 and outer profile of the axle 42 each have a square shape, however, other shapes could be used. Furthermore, an outer surface of the elastomer gasket 108 and the central channel 62 of the inner ring portion 60 of the actuator dial 50 each have a non-circular shape in order to generate the frictional force between the elastomer gasket 108 and the inner ring portion 60 during rotation of the actuator dial 50 due to the elastomeric gasket 108 being compressed/elastically deformed out of its original shape. Similar to the previously described embodiments, increased rotation of the actuator dial 50 proportionally increases the frictional force as the elastomer gasket 108 becomes increasingly elastically deformed away from its initial shape. The friction force holds the cams 68, 70 in place when no load is being applied to the actuator dial 50 by the user, thus maintaining a displacement of the distal tip 16 at any particular position.

Figure 9A:
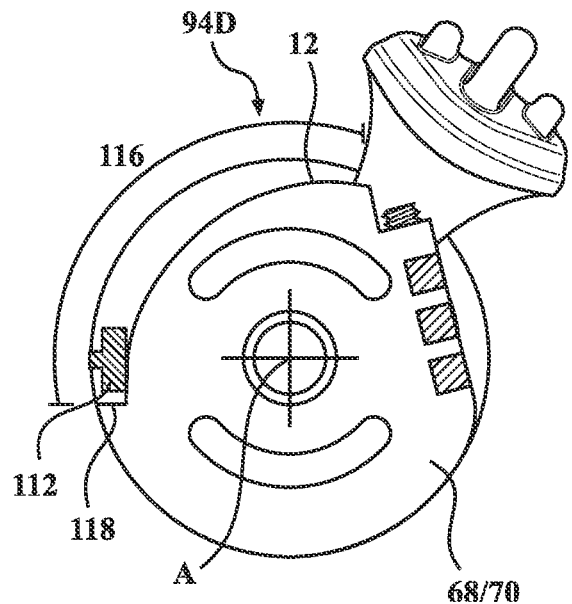
FIG. 9A is a side view of a fifth embodiment of the friction lock illustrating a cam of the friction lock disposed in a first position.
Figure 9B:
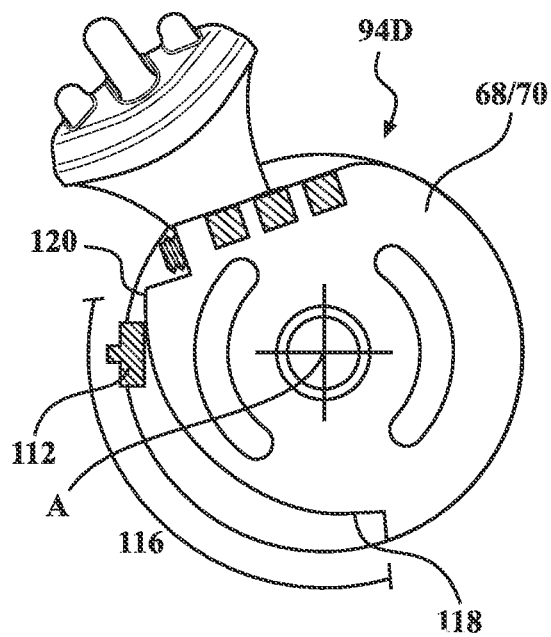
FIG. 9B is a side view of the fifth embodiment of the friction lock, illustrating the cam disposed in a second position.
Figure 9C:
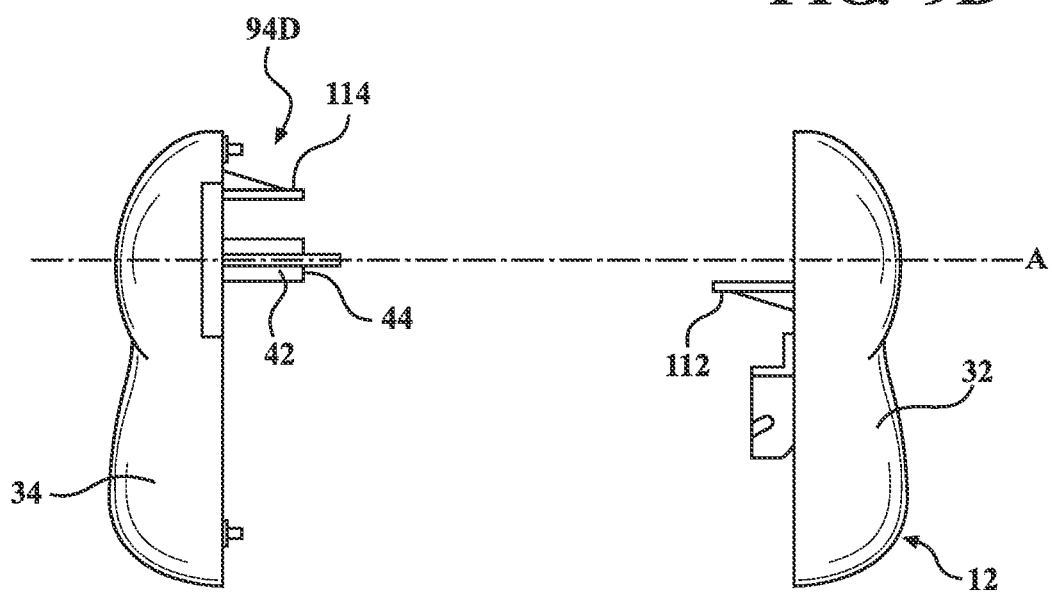
FIG. 9C is a front view of a housing and a pair of friction levers of the fifth embodiment of the friction lock.

In accordance with a fifth embodiment of a friction lock 94D shown in FIGS. 9A-9C, the friction lock 94D includes a first friction lever 112 that extends from the first shell 32 of the housing 12 toward the second shell 34, and a second friction lever 114 that extends from the second shell 34 of the housing toward the first shell 32. The first and second friction levers 112, 114 are each located radially outwardly of the rotational axis A. An outer circumference of each of the cams 68, 70 defines an adjustment region 116 that gradually increases in the radial direction from an inward segment 118 to an outward segment 120. While the cams 68, 70 are positioned in their neutral position, the friction levers 112, 114 are each located along the inward segment 118 of one of the cams 68, 70. As the cams 68, 70 rotate, the friction levers 112, 114 are increasingly biased radially as a point of contact of the friction levers 112, 114 changes from the inward segment 118 to the outward segment 120, thus also providing an increased frictional force. Similar to the previously described embodiments, increased rotation of the actuator dial 50 proportionally increases the frictional force as the friction levers 112, 114 become increasingly biased outwardly. The generated frictional force holds the cams 68, 70 in place when no load is being applied to the actuator dial 50 by the user, thus maintaining a displacement of the distal tip 16 at any particular position.

With reference to FIGS. 10A-13F, various embodiments of a tensioning mechanisms 122E-122H are provided for fixing the wire 38, 40 to the cam 68, 70, and allowing an operator to modify a length of the control wire 38, 40 between the cam 68, 70 and the distal tip 16 in order to provide a base tension of the control wires 38, 40 that correlates with a desired adjustment sensitivity of the control wires 38, 40.

Figure 10A:
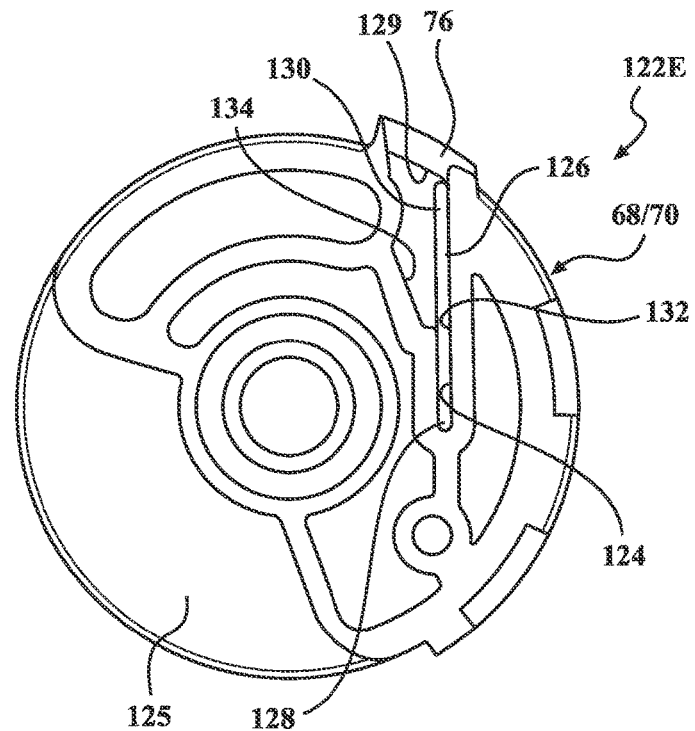
FIG. 10A is a side view of a cam of the steering assembly illustrating a first embodiment of a tensioning mechanism of the endoscope control handle.
Figure 10D:
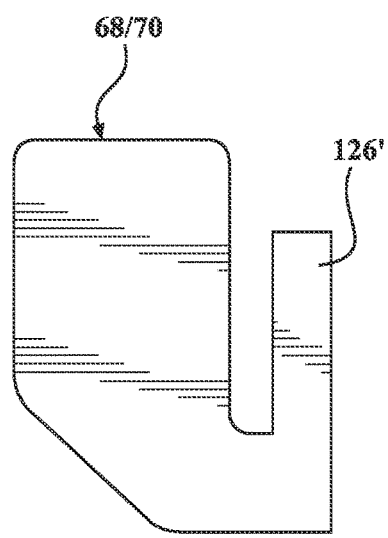
FIG. 10D is a side view of an alternate arrangement of the leaf spring illustrated prior to being bent into a base position during assembly thereof.
Figure 10E:
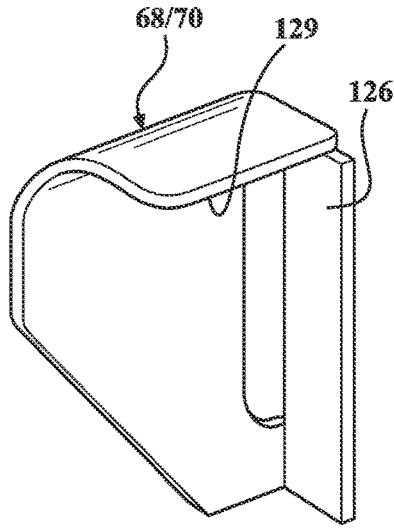
FIG. 10E is a perspective view of the alternate arrangement of the leaf spring illustrated after being bent into the base position during assembly thereof.
Figure 10F:
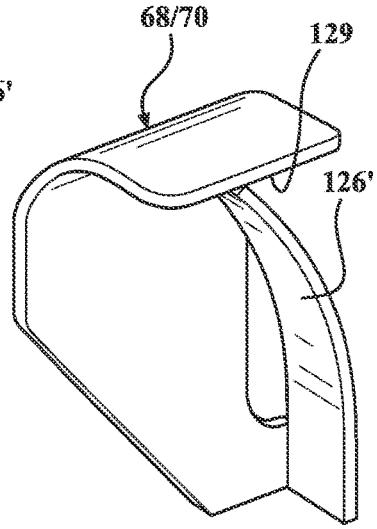
FIG. 10F is a side perspective view of the alternate embodiment of the leaf spring of the first embodiment of the tensioning mechanism, illustrating the leaf spring after a load has been applied thereon by a control wire.
Figure 10B:
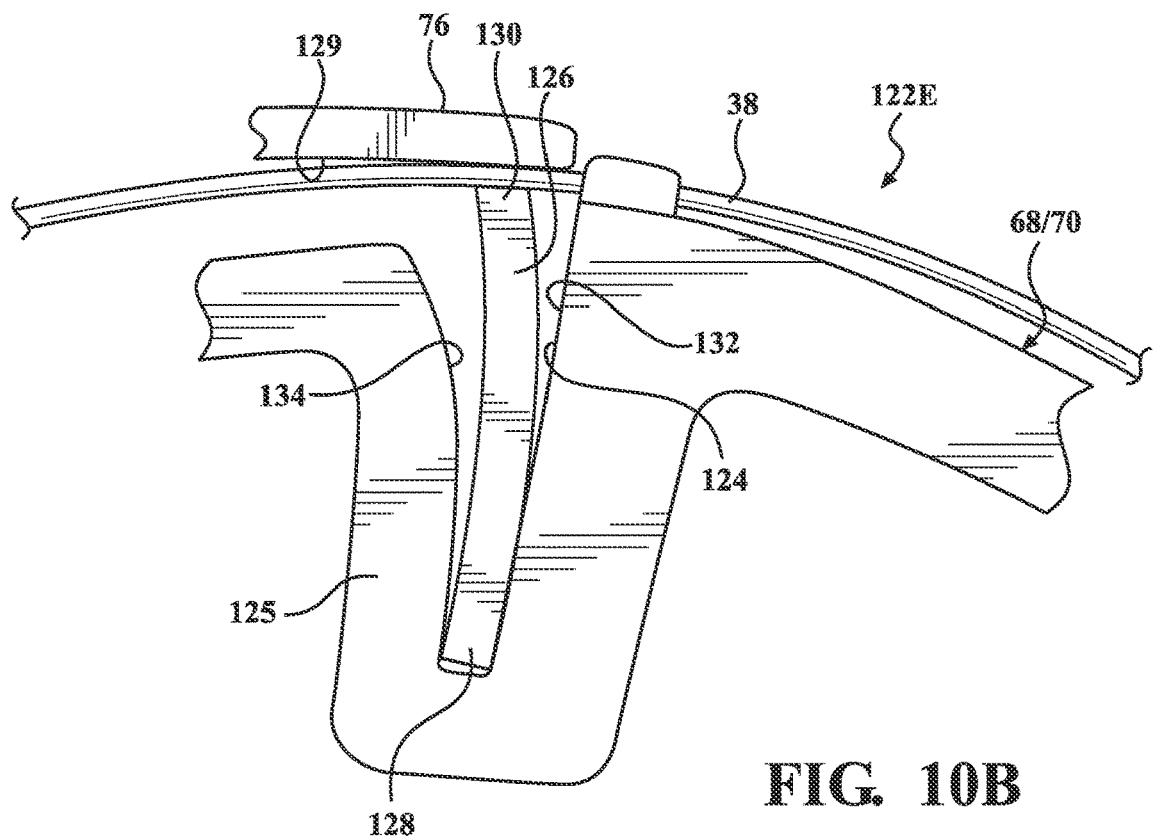
FIG. 10B is a magnified fragmentary side view of the cam illustrating a leaf spring of the first embodiment of the tensioning mechanism disposed in a first position.
Figure 10C:
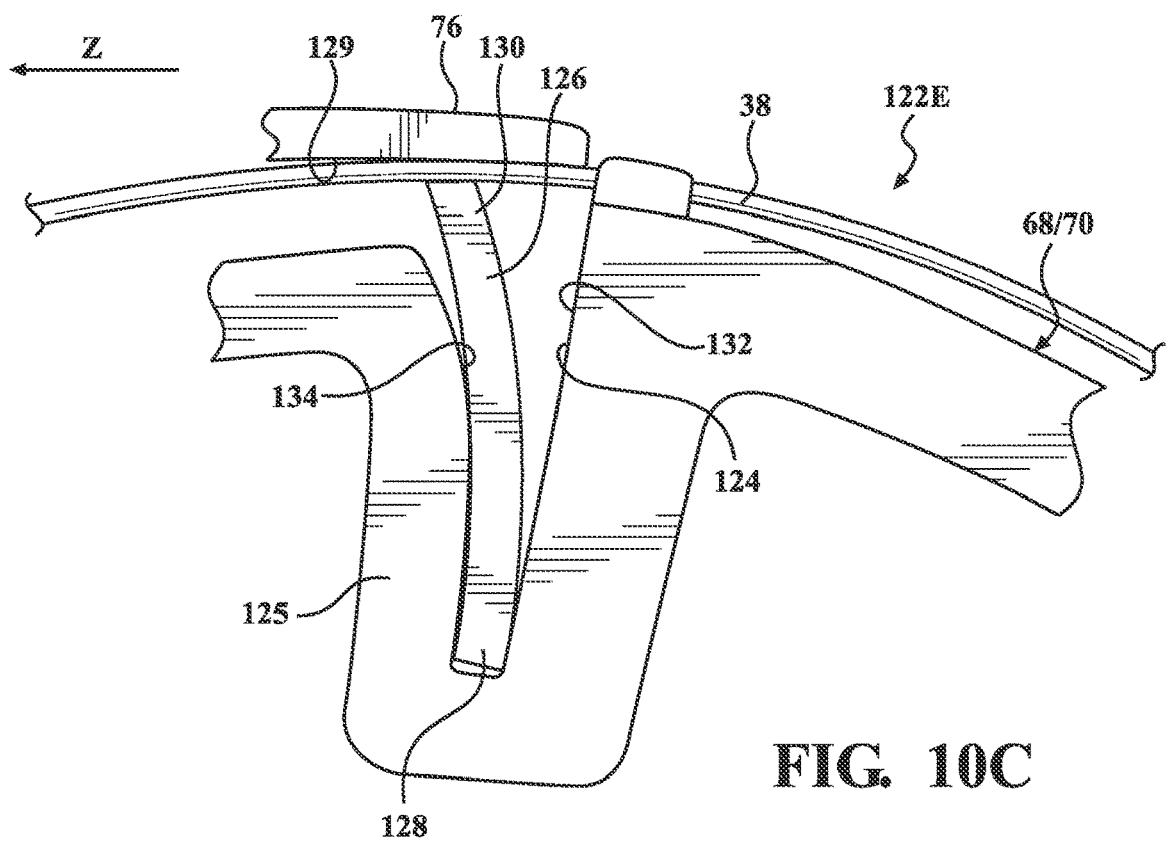
FIG. 10C is a magnified fragmentary side view of the first embodiment of the cam illustrating a leaf spring of the first embodiment of the tensioning mechanism disposed in a second position.

FIGS. 10A-10F disclose a first embodiment of the least one tensioning mechanism 122E. As best shown in FIGS. 10A and 10E-10F, the tensioning mechanism 122 includes a spring pocket 124 that is defined by an axial face 125 of the cam 68, 70. The spring pocket 124 is bounded by a generally planar blocking wall 132 and a deflection wall 134 that extends at an angle from the blocking wall 132. The tensioning mechanism 122 also includes a leaf spring 126 received in the spring pocket 124 at a meeting point of the blocking wall 132 and deflection wall 134. The leaf spring 126 extends from a secured end 128 that is fixed to the respective cam 68, 70 to a biasing end 130 received in one of the tabs 76, with the biasing end 130 biased against a bounding surface 129 of the tab 76, thereby also biasing one of the control wires 38, 40 against the bounding surface 129. The leaf spring 126 is of adequate stiffness to apply a functional load to the bounding surface 129. During use of the control handle 10, the length of the control wire 38, 40 between the cam 68, 70 and the distal tip 16 may be reduced by pulling on the control wire 38, 40 in a tightening direction Z opposite the distal tip 16 (as illustrated in FIG. 10C). The leaf spring 126 is able to flex toward the deflection wall 134, thereby reliving tension of the leaf spring 126 toward the bounding surface 129 and against the wire 38, 40, thus allowing the control wire 38, 40 to be tensioned. After being tensioned, the control wire 38, 40 is unable to move opposite the tightening direction Z because it becomes wedged against the leaf spring 126 and bounding surface 129 in its flexed position, and radially trapped between the leaf spring 126 and tab 76. In a situation in which it is desired to relieve the tension on the control wire 38, 40 and extend the control wire 38, 40, the leaf spring 126 may be manually flexed toward the deflection wall 134, thus providing a gap between the leaf spring 126 and tab 76, allowing movement of the control wire 38, 40 in either direction.

FIGS. 10D-10F illustrate an alternate embodiment of the leaf spring 126' in which the leaf spring 126' is integrally formed with the cam 68, 70 and may be manually assembled or overmolded into the cam 68, 70. FIG. 10D shows the leaf spring 126' with a flat pattern prior to being formed and bent into its neutral position. FIG. 10E presents the leaf spring 126' after being bent into its neutral position. FIG. 10F shows the leaf spring 126' in its finished fabrication form with its biasing end 130 pre-loaded against the bounding surface 129.

Figure 11A:
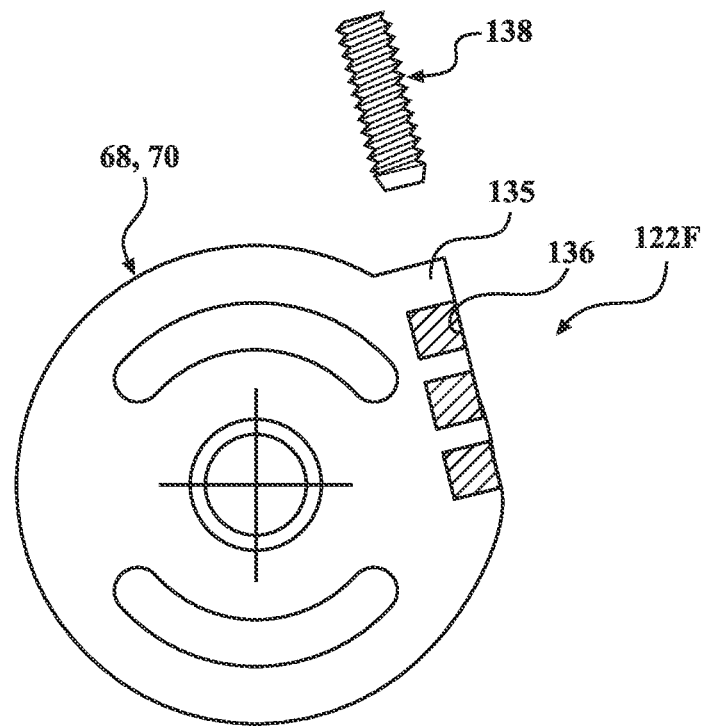
FIG. 11A is a side partially exploded view of a cam according to a second embodiment of a tensioning mechanism, illustrating a tensioning bolt removed from a receptacle of the cam.
Figure 11B:
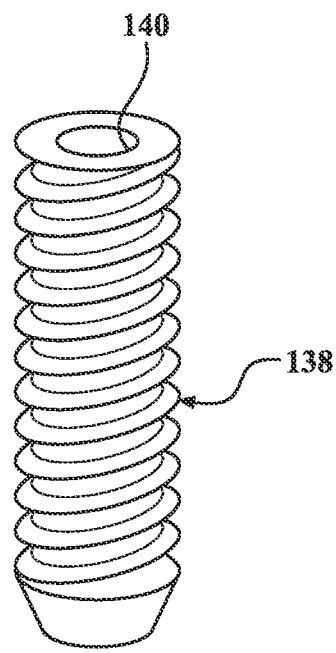
FIG. 11B is a side perspective view of the tensioning bolt.
Figure 11C:
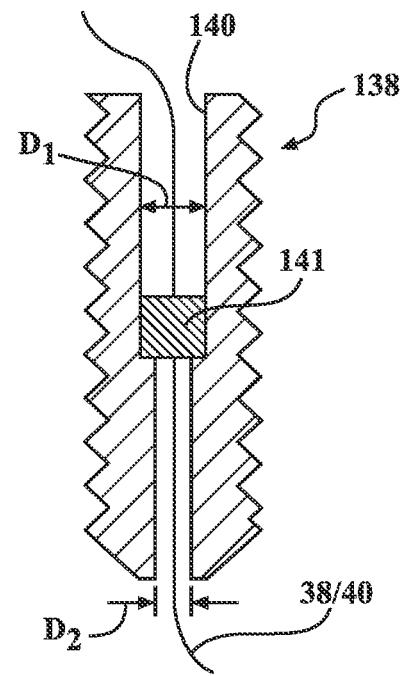
FIG. 11C is a side cutaway view of the tensioning bolt.

FIGS. 11A-11C disclose a second embodiment of the tensioning mechanism 122F. According to this embodiment, the tensioning mechanism 122F includes a receptacle 135 that extends tangentially from an outer circumference of the cam 68, 70 and defines a linear threaded slot 136. The tensioning mechanism 122F also includes a tensioning bolt 138 that is externally threaded and received in the threaded slot 136 of the receptacle 135. The tensioning bolt 138 defines a variable diameter hollow 140 extending therethrough, whereby a first diameter D1 at its proximal end is larger than a second diameter D2 at its distal end, with the second diameter D2 being large enough such that the control wire 28, 30 can pass freely therethrough. The control wire 38, 40 is received by the hollow 140, and a body 141 is crimped along the proximal end of the control wire 38, 40. The body 141 is sized such that it may not pass through the second diameter D2 portion of the hollow 140, thereby limiting its position relative to the tensioning bolt 138. During assembly, the tensioning bolt 138 may be rotated in either direction to tension or loosen the control wire 38, 40 and to balance the tension of both control wires 38, 40 at a neutral position.

Figure 12A:
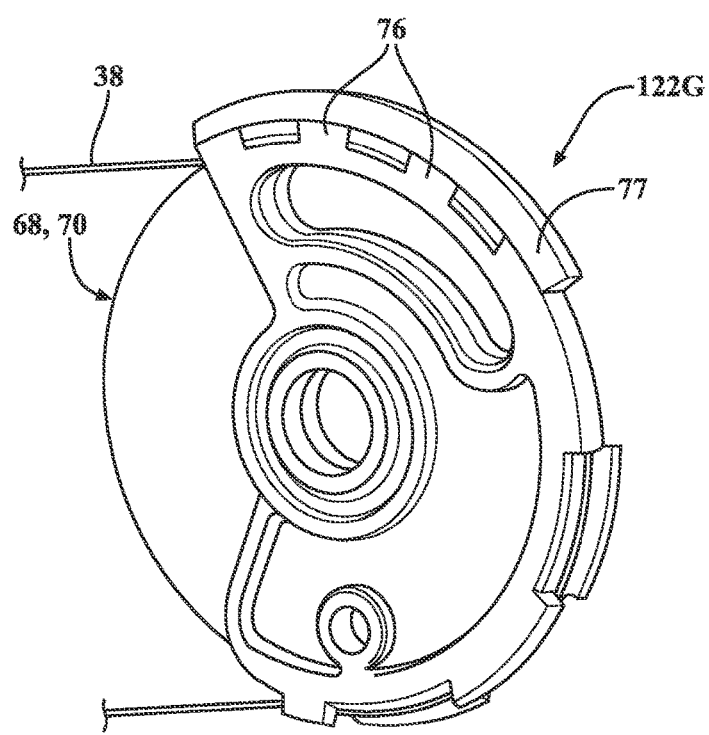
FIG. 12A is a perspective side view of a cam according to a third embodiment of the tensioning mechanism.
Figure 12B:
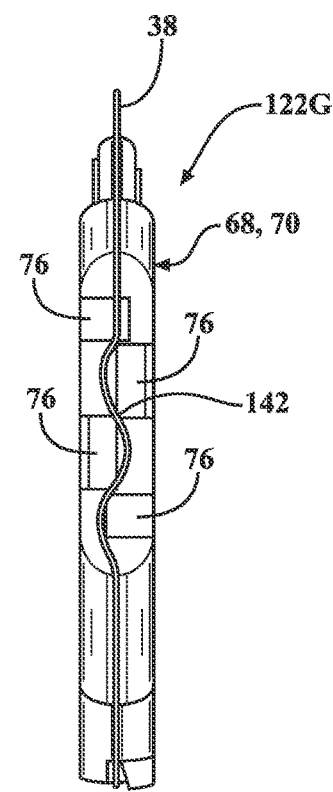
FIG. 12B is a front cutaway view of the cam of the third embodiment of the tensioning mechanism, illustrating a pathway defined by tabs of the cam for receiving a control wire.

FIGS. 12A-12B disclose a third embodiment of the tensioning mechanism 122G. According to this embodiment, the tensioning mechanism is comprised of a labyrinth pathway 142 defined by the plurality of tabs 76 of each of the cams 68, 70 through which the control wire 28, 30 extends. More particularly, the tabs 76 are arranged such that the control wire 28, 30 extends through a series of turns which provides frictional force between the control wire 28, 30 and the tabs 76G that inhibit movement of the control wire 28, 30. Any number of the tabs 76G may make up the labyrinth pathway 142, and the labyrinth pathway 142 may navigate the wire in various directions. During use, once a desired tension is established, the control wire 28, 30 is mechanically deformed such that it fits within the labyrinth pathways 142. In order to relieve tension on the control wire 28, 30 the operator may temporarily remove it from the pathway 142. A removable cap 77 may radially overly the labyrinth pathway 142 to radially close and provide access to the labyrinth pathway.

Figure 13A:
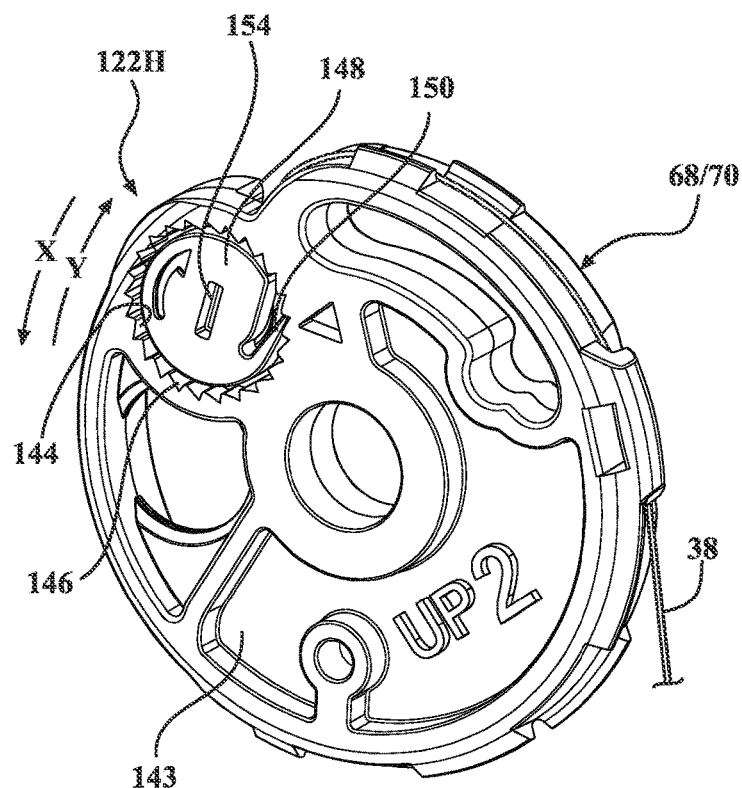
FIG. 13A is a left side perspective view of a cam according to a fourth embodiment of the tensioning mechanism.
Figure 13B:
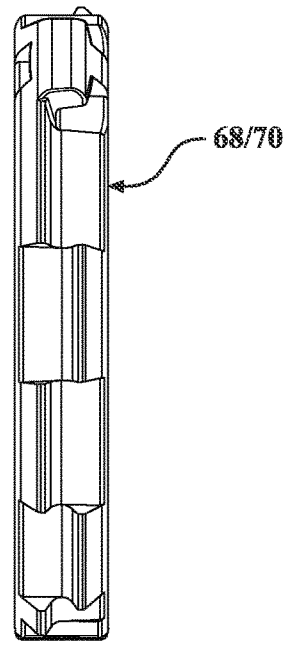
FIG. 13B is a front view of the cam of the fourth embodiment of the tensioning mechanism.
Figure 13C:
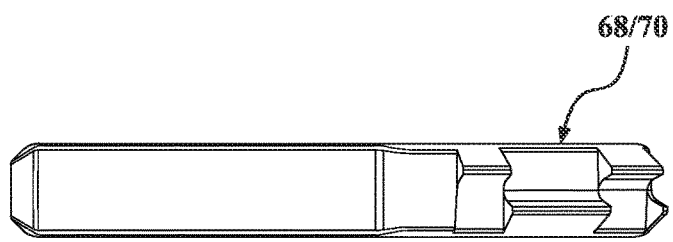
FIG. 13C is a rear view of the cam of the fourth embodiment of the tensioning mechanism.

FIGS. 13A-13F disclose a fourth embodiment of the tensioning mechanism 122H (also shown in FIGS. 2-3). According to this embodiment, an axial face 143 of each of the cams 68, 70 defines a circle-shaped opening 144. As best shown in FIGS. 13A and 13F, a plurality of outer teeth 146 extend radially inwardly into the opening 144. A generally circle-shaped spool 148 is rotationally positioned in the opening 144. As best shown in FIG. 13E, the spool 148 defines a slot 152 that extends generally across a diameter of the spool 148. The control wire 38, 40 extends through the slot 152 such that the control wire 38, 40 is fixed to the spool 148 upon rotation of the spool 148. As best shown in FIG. 13D, the winding surface 75 defines a sloped portion 151 that is aligned with the slot 152 for directing the control wire 38, 40 into the slot. With reference back to FIG. 13A, the spool 148 presents a flexible pawl 150 that extends generally tangentially from an outer circumference of the spool 148 for being received between the outer teeth 146. The spool 148 also defines a tightening element 154 for allowing the spool 148 to be rotated. According to the disclosed embodiment, the tightening element 154 includes a socket that is shaped for receiving a tightening tool, e.g., it may have a hexagonal shape for receiving an allen wrench, or a flat rectangular shape for receiving a screwdriver. With reference to FIG. 13A, in order to tension the control wire 38, 40, the spool 148 is rotated by way of the socket 154 in a first rotational direction (spool direction) Y. The flexible pawl 150 and outer teeth 146 are angled such that attempted rotation in a second rotational direction X opposite the first rotational direction Y results in the pawl 150 engaging one of the outer teeth 146 to inhibit rotation of the spool 148 and to prevent the at least one control wire 38, 40 from unwinding off the spool 148. In order to relieve tension on the control wire 38, 40, the flexible pawl 150 may be held inwardly, preventing it from engaging the outer teeth 146, and rotated in the second rotational direction. The sockets 154 of the spools 148 of the two cams 38, 40 may be axially aligned with the channel 72 of the other cam 38, 40, thereby allowing adjustment of both spools 148 from a single direction.

Obviously, many modifications and variations of the present invention are possible in light of the above teachings and may be practiced otherwise than as specifically described while within the scope of the appended claims. These antecedent recitations should be interpreted to cover any combination in which the inventive novelty exercises its utility. The use of the word "said" in the apparatus claims refers to an antecedent that is a positive recitation meant to be included in the coverage of the claims whereas the word "the" precedes a word not meant to be included in the coverage of the claims.

What is claimed is:

1. A control handle for an interventional device, comprising:
  a housing;
  a tube extending from the housing and terminating at a distal tip;
  at first control wire and a second control wire extending from the housing for termination at the distal tip;
  a steering assembly coupled with the first and second control wires in the housing for selectively tensioning the first and second control wires to effectuate deflecting movement of the distal tip;
  the steering assembly including a first cam and a second cam each rotatable about an axis and presenting a respective winding surface extending circumferentially about the axis;
  the first control wire connected to the first cam and the second control wire connected to the second cam;
  the steering assembly further including an actuator dial rotatable about the axis and disposed axially between the first cam and the second cam;
  the first and second cams each defining a channel disposed radially outwardly of the axis and extending generally arcuately about the axis between a driven end and an undriven end;
  the actuator dial including a first cam follower and a second cam follower each extending axially from opposite axial sides of the actuator dial and each received by and movable within the channel of a respective one of the first or second cams to establish an operably coupled relationship of the actuator dial with the first and second cams;
  wherein rotation of the actuator dial in a first rotational direction moves the first cam follower into engaging relationship with the driven end of the channel of the first cam and correspondingly moves the second cam follower towards the undriven end of the channel of the second cam to rotatably drive the first cam from a neutral position to an actuated position without providing rotational movement of the second cam for at least partially winding the first control wire about the winding surface of the first cam in a first winding direction and deflecting the distal tip in a first deflection direction; and
  wherein rotation of the actuator dial in a second opposite rotational direction moves the second cam follower into engaging relationship with the driven end of the channel of the second cam and correspondingly moves the first cam follower away from the driven end and towards the undriven end of the channel of the first cam to rotatably drive the second cam from a neutral position to an actuated position without providing rotational movement of the first cam for at least partially winding the second control wire around the winding surface of the second cam in a second winding direction arranged opposite the first winding direction and deflecting the distal tip in a second opposite deflecting direction.

2. The control handle as set forth in claim 1 wherein the first and second cam followers are axially aligned with one another and wherein the driven end of the channel of the first cam is circumferentially offset from the undriven end of the channel of the second cam at a predetermined angle (θ1) in the neutral position.

3. The control handle as set forth in claim 2 wherein the actuator dial, the first cam and the second cam each define an alignment hole collectively disposed in axially aligned relationship with one another when the actuator dial, the first cam and the second cam are in the neutral position, and an alignment pin is received by the alignment holes during assembly to locate the actuator dial, the first cam and the second cam in the neutral position during assembly.

4. The control handle as set forth in claim 1, further including a friction lock frictionally interlockable with the first cam during rotation of the actuator dial in the first rotational direction and frictionally interlockable with the second cam during rotation of the actuator dial in the second rotational direction for preventing the first and second cams from freely rotating from their respective actuated position back to the neutral position and releasing tension on the respective first and second control wires without associated movement of the actuator dial by the user.

5. The control handle as set forth in claim 4, wherein the actuator dial defines a central channel aligned on the axis, and the friction lock includes a thrust bearing rotationally fixed and threadedly received by the central channel such that rotation of the actuator dial about the axis effectuates axial movement of the thrust bearing towards one of the first or second cams to establish a bias of the respective first or second cam towards the housing to establish the frictional interlocking relationship of the first and second cams.

6. The control handle as set forth in claim 5, wherein the friction lock further includes a first compression element disposed between the first cam and the housing and a second compression element disposed between the second cam and the housing such that axial movement of the thrust bearing into abutting relationship with the first or second cam causes the respective first compression element or second compression element to engage the housing to create the frictional interlocking relationship of the first or second cam.

7. The control handle as set forth in claim 6, wherein the first and second compression elements are wave washers.

8. The control handle as set forth in claim 5, further comprising an axle fixed to the housing and extending along the axis, and wherein the thrust bearing is keyed to the axle to prevent rotational movement of the thrust bearing while allowing axial movement of the thrust bearing in response to rotation of the actuator dial.

9. The control handle as set forth in claim 4, wherein a thumb grip is connected to an outer circumference of the actuator dial and located outside of the housing for allowing a user to rotate the actuator dial.

10. The control handle as set forth in claim 1, wherein said first and second cams each include at least one tensioning mechanism receiving the first or second control wire for establishing the connected relationship between the first and second control wire and the respective first and second cams, and said at least one tensioning mechanism adjustable for allowing an operator to modify a length of the first and second control wires between the first and second cams and the distal tip.

11. The control handle as set forth in claim 10, wherein the at least one tensioning mechanism includes a spool rotatably connected to the first and second cams and including a pawl configured to allow free rotation of the spool in a first rotational spool direction for selectively shortening the first and second control wires between the first and second cams and the distal tip while preventing rotation of the spool in a second rotational spool direction opposite the first rotational spool direction for preventing the first and second control wires from being lengthened from their shortened conditions.

12. The control handle as set forth in claim 11, wherein an axial face of the first and second cams defines an opening presenting a plurality of teeth extending radially inwardly into the opening, and the pawl extends from a circumference of the spool and is configured to bypass the plurality of teeth during rotation of the spool in the first rotational direction, and to engage at least one of the teeth in response to biasing of the spool in the second rotational direction to prevent the spool from rotating.

13. The control handle as set forth in claim 11, wherein the spool defines a slot extending diametrically across the spool for receiving the first and second control wires and securing the first and second control wires to the respective spool.

14. The control handle as set forth in claim 11, wherein the spool includes a tightening element for allowing a user to rotate the spool.

15. The control handle as set forth in claim 14, wherein the tightening element is a socket defined by an axial face of the spool for receiving a tightening tool.

16. A control handle for an interventional device, comprising:
a housing;
a tube extending from the housing and terminating at a distal tip;
at least one control wire extending from the housing for termination at the distal tip;
a steering assembly coupled with the at least one control wire in the housing for selectively tensioning the at least one control wire to effectuate movement of the distal tip;
the steering assembly including at least one cam rotatable about an axis and presenting a winding surface extending circumferentially about the axis;
the at least one control wire connected to the at least one cam;
the steering assembly further including an actuator dial rotatable about the axis and operably coupled with the at least one cam for rotatably driving the at least one cam from a neutral position to an actuated position to at least partially wind the at least one control wire about the winding surface and tension the at least one control wire for deflecting the distal tip in response to rotation of the actuator dial by a user;
a friction lock frictionally interlockable with the at least one cam during rotation of the actuator dial for preventing the at least one cam from freely rotating from the actuated position back to the neutral position and releasing tension on the at least one control wire without associated movement of the actuator dial by the user;
the actuator dial defining a central channel aligned on the axis, and
the friction lock includes a thrust bearing rotationally fixed and threadedly received by the central channel such that rotation of the actuator dial about the axis effectuates axial movement of the thrust bearing towards the at least one cam to establish a bias of the at least one cam towards the housing to establish the frictional interlocking relationship of the at least one cam.

17. The control handle as set forth in claim 16, wherein the friction lock further includes a compression element disposed between the at least one cam and the housing such that axial movement of the thrust bearing into abutting relationship with the at least one cam causes the compression element to engage the housing to create the frictional interlocking relationship of the at least one cam.

18. The control handle as set forth in claim 17, wherein the compression element is a wave washer.

19. The control handle as set forth in claim 16, further comprising an axle fixed to the housing and extending along the axis, and wherein the thrust bearing is keyed to the axle to prevent rotational movement of the thrust bearing while allowing axial movement of the thrust bearing in response to rotation of the actuator dial.

* * * * *